US010265424B2

(12) United States Patent
Rychak et al.

(10) Patent No.: US 10,265,424 B2
(45) Date of Patent: Apr. 23, 2019

(54) MOLECULAR IMAGING CONTRAST AGENTS AND USES THEREOF

(71) Applicant: Trust-Biosonics, Inc., Hsinchu County (TW)

(72) Inventors: Joshua L. Rychak, Oceanside, CA (US); Alice Luong, San Diego, CA (US)

(73) Assignee: Trust-Biosonics, Inc., Hsinchu County (TW)

( * ) Notice: Subject to any disclaimer, the term of this patent is extended or adjusted under 35 U.S.C. 154(b) by 334 days.

(21) Appl. No.: 14/639,055

(22) Filed: Mar. 4, 2015

(65) Prior Publication Data

US 2015/0250903 A1 Sep. 10, 2015

Related U.S. Application Data

(60) Provisional application No. 61/966,875, filed on Mar. 4, 2014.

(51) Int. Cl.

| | |
|---|---|
| *A61K 49/00* | (2006.01) |
| *C07K 17/00* | (2006.01) |
| *A61K 49/22* | (2006.01) |
| *A61K 41/00* | (2006.01) |
| *A61M 37/00* | (2006.01) |
| *A61K 49/14* | (2006.01) |
| *A61K 51/08* | (2006.01) |
| *A61K 47/64* | (2017.01) |
| *A61K 47/68* | (2017.01) |

(52) U.S. Cl.
CPC ........ *A61K 49/221* (2013.01); *A61K 41/0028* (2013.01); *A61K 47/64* (2017.08); *A61K 47/68* (2017.08); *A61K 49/0056* (2013.01); *A61K 49/14* (2013.01); *A61K 49/223* (2013.01); *A61K 49/227* (2013.01); *A61K 51/08* (2013.01); *A61M 37/0092* (2013.01)

(58) Field of Classification Search
None
See application file for complete search history.

(56) References Cited

U.S. PATENT DOCUMENTS

| | | | | |
|---|---|---|---|---|
| 2010/0196284 | A1* | 8/2010 | Lindner | A61K 9/0009 424/9.52 |
| 2012/0183475 | A1* | 7/2012 | Michel | A61K 49/0438 424/9.1 |
| 2012/0244078 | A1* | 9/2012 | Rychak | A61K 49/0002 424/9.6 |
| 2013/0156706 | A1* | 6/2013 | Bettinger | A61K 49/222 424/9.52 |
| 2014/0134102 | A1* | 5/2014 | Michel | A61K 49/0438 424/1.11 |

FOREIGN PATENT DOCUMENTS

WO    WO9744460    * 11/1997

OTHER PUBLICATIONS

Donnarumma, Tiziano, TIM-1 is a physiological P-selectin ligand that mediates T-cell trafficking during inflammation. Universita' Degli Studi Di Verona. Department of Pathology and Diagnostic—Division of General Pathology. Doctoral Thesis, 2011, pp. 1-110.*
Fokong et al. Ultrasound Molecular Imaging of E-Selectin in Tumor Vessels Using Poly n-Butyl Cyanoacrylate Microbubbles Covalently Coupled to a Short Targeting Peptide. Invest Radiol 2013;48: 843-850.*
Szabo et al. Molecular Imaging of the Kidneys. Semin Nucl Med. Jan. 1, 2011; 41(1): 20-28.*
Deshpande et al, Quantification and Monitoring of Inflammation in Murine Inflammatory Bowel Disease with Targeted Contrast-enhanced US. Radiology. Jan. 2012; 262(1): 172-180.*
Kevin M. Bennett. Molecular Magnetic Resonance Imaging of the Kidney. MI Gateway; Sep. 2011, p. 1-4.*
Davidson et al. Detection of Antecedent Myocardial Ischemia With Multiselectin Molecular Imaging. J Am Coll Cardiol. Oct. 23, 2012; 60(17):1-15.*
Rychak et al. Selectin Ligands Promote Ultrasound Contrast Agent Adhesion under Shear Flow. Molecular Pharmaceutics vol. 3, No. 5, 516-524.*
Klibanov, AL., Ligand-Carrying Gas-Filled Microbubbles: Ultrasound Contrast Agents for Targeted Molecular Imaging. Bioconjugate Chem. 2005, 16, 9-17 (Year: 2005).*
McIntire et al. Identification of Tapr (an airway hyperreactivity regulatory locus) and the linked Tim gene family. Nat Immunol. Dec. 2001;2(12):1109-16. (Year: 2001).*
Lin et al. Murine Tim-1 is excluded from the immunological synapse. Version 2. F1000Res. 2012; 1: 10. Published online Oct. 10, 2012. (Year: 2012).*
Ichimura et al. Kidney injury molecule-1 is a phosphatidylserine receptor that confers a phagocytic phenotype on epithelial cells. J. Clin. Invest. 118:1657-1668 (2008). (Year: 2008).*
Lingadahalli, Shreyas, "Activated Neutrophils Mediate KIM-1 Shedding and Renal Remodelling" (2013). ETD Archive. Paper 558. (Year: 2013).*
Lindner, Jonathan R., Contrast ultrasound molecular imaging of inflammation in cardiovascular disease. (Cardiovascular Research (2009) 84, 182-189) (Year: 2009).*
Klibanov AL Targeted ultrasound contrast agent for molecular imaging of inflammation in high-shear flow. Contrast Media Mol Imaging. Nov.-Dec. 2006;1(6):259-66. (Year: 2006).*

* cited by examiner

Primary Examiner — Maher M Haddad
(74) Attorney, Agent, or Firm — Chang-Hsing Liang

(57) ABSTRACT

Compositions and methods for molecular imaging of selectins are disclosed. Specifically, compositions comprising medical imaging contrast-producing agents associated with the extracellular domain of TIM-1 as a targeting ligand for use in molecular imaging of selectins are disclosed. Also, methods of using the extracellular domain of TIM-1 as a ligand for achieving specific targeting to selectins as therapeutic drug delivery vehicles is also disclosed.

5 Claims, 7 Drawing Sheets

Specification includes a Sequence Listing.

|  | 10 | 20 | 30 | 40 | 50 | 60 |
|---|---|---|---|---|---|---|
| MHPQVVILSL | ILHLADSVAG | SVKVGGEAGP | SVTLPCHYSG | AVTSMCWNRG | SCSLFTCQNG |

|  | 70 | 80 | 90 | 100 | 110 | 120 |
|---|---|---|---|---|---|---|
| IVWTNGTHVT | YRKDTRYKLL | GDLSRRDVSL | TIENTAVSDS | GVYCCRVEHR | GWFNDMKITV |

|  | 130 | 140 | 150 | 160 | 170 | 180 |
|---|---|---|---|---|---|---|
| SLEIVPPKVT | TTPIVTTVPT | VTTVRTSTTV | PTTTTVPTTT | VPTTMSIPTT | TTVLTTMTVS |

|  | 190 | 200 | 210 | 220 | 230 | 240 |
|---|---|---|---|---|---|---|
| TTTSVPTTTS | IPTTTSVPVT | TTVSTFVPPM | PLPRQNHEPV | ATSPSSPQPA | ETHPTTLQGA |

|  | 250 | 260 | 270 | 280 | 290 | 300 |
|---|---|---|---|---|---|---|
| IRREPTSSPL | YSYTTDGNDT | VTESSDGLWN | NNQTQLFLEH | SLLTANTTKG | IYAGVCISVL |

|  | 310 | 320 | 330 | 340 | 350 |
|---|---|---|---|---|---|
| VLLALLGVII | AKKYFFKKEV | QQLSVSFSSL | QIKALQNAVE | KEVQAEDNIY | IENSLYATD |

Figure 1

SEQUENCE LISTING

```
<160> NUMBER OF SEQ ID NOS: 3

<210> SEQ ID NO 1
<211> LENGTH: 359
<212> TYPE: PRT
<213> ORGANISM: Homo sapiens

<400> SEQUENCE: 1
```

```
Met His Pro Gln Val Val Ile Leu Ser Leu Ile Leu His Leu Ala Asp
1               5                   10                  15

Ser Val Ala Gly Ser Val Lys Val Gly Glu Ala Gly Pro Ser Val
            20                  25                  30

Thr Leu Pro Cys His Tyr Ser Gly Ala Val Thr Ser Met Cys Trp Asn
        35                  40                  45

Arg Gly Ser Cys Ser Leu Phe Thr Cys Gln Asn Gly Ile Val Trp Thr
50                  55                  60

Asn Gly Thr His Val Thr Tyr Arg Lys Asp Thr Arg Tyr Lys Leu Leu
65              70                  75                  80

Gly Asp Leu Ser Arg Arg Asp Val Ser Leu Thr Ile Glu Asn Thr Ala
                85                  90                  95

Val Ser Asp Ser Gly Val Tyr Cys Cys Arg Val Glu His Arg Gly Trp
                100                 105                 110

Phe Asn Asp Met Lys Ile Thr Val Ser Leu Glu Ile Val Pro Pro Lys
            115                 120                 125

Val Thr Thr Thr Pro Ile Val Thr Thr Val Pro Thr Val Thr Thr Val
    130                 135                 140

Arg Thr Ser Thr Thr Val Pro Thr Thr Thr Val Pro Thr Thr Thr
145                 150                 155                 160

Val Pro Thr Thr Met Ser Ile Pro Thr Thr Thr Val Leu Thr Thr
                165                 170                 175

Met Thr Val Ser Thr Thr Thr Ser Val Pro Thr Thr Thr Ser Ile Pro
        180                 185                 190

Thr Thr Thr Ser Val Pro Val Thr Thr Thr Val Ser Thr Phe Val Pro
            195                 200                 205

Pro Met Pro Leu Pro Arg Gln Asn His Glu Pro Val Ala Thr Ser Pro
    210                 215                 220

Ser Ser Pro Gln Pro Ala Glu Thr His Pro Thr Thr Leu Gln Gly Ala
225                 230                 235                 240

Ile Arg Arg Glu Pro Thr Ser Ser Pro Leu Tyr Ser Tyr Thr Thr Asp
                245                 250                 255

Gly Asn Asp Thr Val Thr Glu Ser Ser Asp Gly Leu Trp Asn Asn Asn
                260                 265                 270

Gln Thr Gln Leu Phe Leu Glu His Ser Leu Leu Thr Ala Asn Thr Thr
        275                 280                 285

Lys Gly Ile Tyr Ala Gly Val Cys Ile Ser Val Leu Val Leu Leu Ala
        290                 295                 300

Leu Leu Gly Val Ile Ile Ala Lys Lys Tyr Phe Phe Lys Lys Glu Val
305                 310                 315                 320

Gln Gln Leu Ser Val Ser Phe Ser Ser Leu Gln Ile Lys Ala Leu Gln
                325                 330                 335

Asn Ala Val Glu Lys Glu Val Gln Ala Glu Asp Asn Ile Tyr Ile Glu
                340                 345                 350

Asn Ser Leu Tyr Ala Thr Asp
        355

<210> SEQ ID NO 2
<211> LENGTH: 270
<212> TYPE: PRT
<213> ORGANISM: Homo sapiens

<400> SEQUENCE: 2

Ser Val Lys Val Gly Gly Glu Ala Gly Pro Ser Val Thr Leu Pro Cys
```

```
              1               5                  10                 15
            His Tyr Ser Gly Ala Val Thr Ser Met Cys Trp Asn Arg Gly Ser Cys
                        20                  25                 30

Ser Leu Phe Thr Cys Gln Asn Gly Ile Val Trp Thr Asn Gly Thr His
                        35                  40                 45

Val Thr Tyr Arg Lys Asp Thr Arg Tyr Lys Leu Leu Gly Asp Leu Ser
                        50                  55                 60

Arg Arg Asp Val Ser Leu Thr Ile Glu Asn Thr Ala Val Ser Asp Ser
            65                      70                  75                 80

Gly Val Tyr Cys Cys Arg Val Glu His Arg Gly Trp Phe Asn Asp Met
                                85                  90                 95

Lys Ile Thr Val Ser Leu Glu Ile Val Pro Pro Lys Val Thr Thr Thr
                            100                 105                110

Pro Ile Val Thr Thr Val Pro Thr Val Thr Thr Val Arg Thr Ser Thr
                            115                 120                125

Thr Val Pro Thr Thr Thr Thr Val Pro Thr Thr Thr Val Pro Thr Thr
                            130                 135                140

Met Ser Ile Pro Thr Thr Thr Val Pro Thr Thr Met Thr Val Ser
            145                     150                 155                160

Thr Thr Thr Ser Val Pro Thr Thr Thr Ser Ile Pro Thr Thr Thr Ser
                            165                 170                175

Val Pro Val Thr Thr Thr Val Ser Thr Phe Val Pro Pro Met Pro Leu
                            180                 185                190

Pro Arg Gln Asn His Glu Pro Val Ala Thr Ser Pro Ser Ser Pro Gln
                            195                 200                205

Pro Ala Glu Thr His Pro Thr Thr Leu Gln Gly Ala Ile Arg Arg Glu
                            210                 215                220

Pro Thr Ser Ser Pro Leu Tyr Ser Tyr Thr Thr Asp Gly Asn Asp Thr
            225                     230                 235                240

Val Thr Glu Ser Ser Asp Gly Leu Trp Asn Asn Asn Gln Thr Gln Leu
                            245                 250                255

Phe Leu Glu His Ser Leu Leu Thr Ala Asn Thr Thr Lys Gly
                            260                 265                270

<210> SEQ ID NO 3
<211> LENGTH: 275
<212> TYPE: PRT
<213> ORGANISM: Homo sapiens

<400> SEQUENCE: 3

Ser Val Lys Val Gly Gly Glu Ala Gly Pro Ser Val Thr Leu Pro Cys
            1                5                   10                 15

His Tyr Ser Gly Ala Val Thr Ser Met Cys Trp Asn Arg Gly Ser Cys
                        20                  25                 30

Ser Leu Phe Thr Cys Gln Asn Gly Ile Val Trp Thr Asn Gly Thr His
                        35                  40                 45

Val Thr Tyr Arg Lys Asp Thr Arg Tyr Lys Leu Leu Gly Asp Leu Ser
                        50                  55                 60

Arg Arg Asp Val Ser Leu Thr Ile Glu Asn Thr Ala Val Ser Asp Ser
            65                      70                  75                 80

Gly Val Tyr Cys Cys Arg Val Glu His Arg Gly Trp Phe Asn Asp Met
                                85                  90                 95

Lys Ile Thr Val Ser Leu Glu Ile Val Pro Pro Lys Val Thr Thr Thr
                            100                 105                110
```

```
Pro Ile Val Thr Thr Val Pro Thr Val Thr Thr Val Arg Thr Ser Thr
        115                 120                 125
Thr Val Pro Thr Thr Thr Thr Val Pro Thr Thr Thr Val Pro Thr Thr
        130                 135                 140
Met Ser Ile Pro Thr Thr Thr Thr Val Pro Thr Thr Met Thr Val Ser
145                 150                 155                 160
Thr Thr Thr Ser Val Pro Thr Thr Ser Ile Pro Thr Thr Thr Ser
                165                 170                 175
Val Pro Val Thr Thr Thr Val Ser Thr Phe Val Pro Pro Met Pro Leu
                180                 185                 190
Pro Arg Gln Asn His Glu Pro Val Ala Thr Ser Pro Ser Ser Pro Gln
            195                 200                 205
Pro Ala Glu Thr His Pro Thr Thr Leu Gln Gly Ala Ile Arg Arg Glu
            210                 215                 220
Pro Thr Ser Ser Pro Leu Tyr Ser Tyr Thr Thr Asp Gly Asn Asp Thr
225                 230                 235                 240
Val Thr Glu Ser Ser Asp Gly Leu Trp Asn Asn Asn Gln Thr Gln Leu
                245                 250                 255
Phe Leu Glu His Ser Leu Leu Thr Ala Asn Thr Thr Lys Gly Ile Tyr
            260                 265                 270
Ala Gly Val
        275
```

MOLECULAR IMAGING CONTRAST AGENTS AND USES THEREOF

CROSS-REFERENCE TO RELATED APPLICATIONS

This application claims the benefit of priority to U.S. Provisional Application No. 61/966,875 filed on Mar. 4, 2014, the contents of which is incorporated herein by reference.

BACKGROUND OF THE INVENTION

Molecular Imaging and Therapy

The current invention pertains to agents for use in molecular imaging and therapy. Molecular imaging uses exogenous contrast agents administered to the patient, whose presence within the body can be detected using medical imaging techniques. Molecular contrast agents comprise a medical imaging contrast agent bound to a targeting ligand. The contrast agent is the contrast-producing substance that is detectible by medical imaging, while the ligand is responsible for binding of the agent to the intended molecular target within the body.

Many potential targets for molecular imaging have been discovered in recent years. Similarly, the field boasts a wealth of medical imaging contrast agents able to be detected by all established medical imaging techniques. However, a key challenge in the field remains identification of suitable ligands for a given target. Specificity for the intended target is of paramount importance. Affinity and on-rate of binding are important for intravascular contrast agents. In addition, the suitability of a given ligand for conjugation to a contrast agent is important. The ability to produce a ligand at high purity and high volume is also critical. Finally, the absence of immunogenicity is desired. For each of these reasons, targeting ligands derived from or based on endogenously occurring human proteins can offer significant benefits.

Selectins as Molecular Markers of Disease

Selectins are carbohydrate-binding transmembrane molecules expressed on endothelial cells, platelets and leukocytes. They have an N-terminal C-type lectin domain. Two members of the selectin family have particular relevance in the context of molecular imaging: P-selectin and E-selectin. Up-regulation or expression of P- and E-selectin on the vascular endothelium is known to occur under conditions of inflammation, while the presence of endothelial selectins under resting conditions is generally low to nil. Disease states in which selectins are useful molecular imaging targets include post-ischemic injury, acute coronary syndrome, arthritis, inflammatory bowel disease including ileitis and colitis, atherosclerosis, myocarditis, thrombosis and multiple sclerosis. Selectin molecular imaging may be useful to deliniate and identify tissues in which selectin expression occurs under normal conditions, such as the skin microvasculature.

Up-regulation of P-selectin (CD62P) is known to occur very rapidly (within minutes), making P-selectin a potential marker of early stages of inflammatory disease. P-selectin is also found on the surface of activated platelets, making it a marker of thrombosis.

E-selectin (CD62E) is also expressed on inflamed vasculature, although generally later in the inflammatory response than P-selectin. E-selectin is thus a useful marker of inflammation at later stages of the disease.

Robust detection of inflammatory disease may be accomplished through the use of a molecular imaging probe able to detect both P- and E-selectin. Thus, it is desirable in many cases for an imaging agent intended for detecting inflammation to exhibit reactivity for both P- and E-selectins.

Differential expression of P- and E-selectin is found in some disease states. A molecular imaging agent able to bind either P- or E-selectin may be broadly useful for imaging a wide variety of disease states.

There is prior art pertaining to the use of selectins as a molecular imaging target. Use of selectins as imaging targets is contemplated, for example, in U.S. Pat. No. 6,139,819 (Unger et al); U.S. Pat. No. 6,680,047 (Klaveness et al) and U.S. Pat. No. 6,254,852 (Glajch et al). Lindner (Circulation, 2001) conjugated a rat-anti-mouse P-selectin antibody to a microbubble contrast agent and demonstrated successful detection of post-ischemic kidney injury in mice. Other studies have demonstrated use of selectins as imaging targets for detection of inflammatory bowel disease (Deshpande et al, Radiology 2012), post-ischemic myocardial injury (Villanueva et al, Circulation 2007; Leng et al, 2014), and thrombosis (Guenther et al, Invest Radiol 2010). P-selectin has also been used as a target for targeted drug delivery, for example Xie et al (J. Am. Coll. Cardiol. 2012).

Selectin-Binding Ligands

Several classes of molecules have been contemplated as ligands for imaging of selectins. Antibodies, including Fab fragments, Fv fragments, single chain molecules, and humanized anti-human antibodies, have been contemplated in this regard.

Synthetic (not naturally occurring) peptides with affinity for selectins have been described, for example in U.S. Pat. No. 5,643,873 (Barrett et al), U.S. Pat. No. 7,470,658 (Fukuda et al). Several of these have been contemplated for molecular imaging: Funovics et al (Neoplasia 2005), Zinn et al (Arthritis and Rheumatism, 1999), Gratz et al (Nuc. Ned. Comm, 2001) and Jinn et al (Cont. Med. Mol. Imaging, 2009).

Another class of ligands comprises structures based on the known endogenous selectin ligands. PSGL-1 is the most well characterized selectin ligand. PSGL-1 is a cell surface protein that exists as a dimer and contains extensive O-linked glycosylation. Various forms of PSGL-1 have been contemplated as ligands for selectin imaging, for example Davidson et al (J. Am Coll. Cardiol, 2012), and International (PCT) Publication No. WO2008131217A1 (Lindner et al). Fragments of the PSGL-1 protein have also been contemplated in this regard, for example in International (PCT) Publication No. WO2012020030A1 (Bettinger et al), Rychak et al (Mol. Pharm 2006), and Deshpande et al, (Radiology, 2012).

Various carbohydrate-based structures, some of which are components of PSGL-1, are also known to bind to selectins. This class of molecules has also been contemplated as ligands for imaging selectins, for example Villanueva et al (Circulation, 2007), Klibanov et al (Cont. Med. Mol. Imaging, 2006), and Rouzet et al (J. Nuc. Med, 2011).

TIM-1

T-cell Ig domain and mucin domain (TIM) is a family of transmembrane proteins expressed on various immune cell types, in addition to kidney and liver. Members of the TIM family are known to be involved primarily in regulation of autoimmunity (Rodriguez-Manzanet et al, 2009), although relevance in other disease processes (for example, kidney injury) has been reported (U.S. Pat. No. 6,664,385).

Of particular relevance to the current application is TIM-1 (also known as HAVCR1 (gene name), hepatitis A virus cellular receptor 1; KIM1; TIM1; HAVCR; KIM-1; TIMD1; TIMD-1; HAVCR-1). TIM-1 is a transmembrane molecule expressed on many leukocyte types, including mast cells, naïve CD4+ lymphocytes, NK cells, and some B-cells. TIM-1 is also expressed on, and shed from, renal epithelial cells in the context of kidney injury.

TIM-1 is known to bind to four molecules: TIM-1 itself, TIM-4, IGA-lambda, and phosphatidylserine. No affinity for lectins or similar molecules (including selectins), is documented in the prior art.

We have made the surprising observation that the extracellular domain of TIM-1, when conjugated to a contrast-producing agent, mediates high affinity and specific binding to selectins. As such, the extracellular domain of TIM-1 is useful for use as a ligand in the context of molecular imaging of diseases in which selectin expression is present.

The extracellular portion of TIM-1 has an N-terminal Ig-like V domain followed by a long mucin domain. The deduced amino acid sequence of human TIM-1 is shown in FIG. 1 and SEQ ID NO: 1.

Amino acids (AA) 1-20 are the signal peptide, AA 21-290 are the extracellular domain, AA 291-311 are the helical transmembrane domain and AA 312-359 are the cytoplasmic domain. Within the extracellular domain, AA 21-121 are an Ig-like V-type domain. AA 138-202 encode 11 repeats of 5 or 6 AA that encode the mucin domain. AA 203-290 encode a membrane-proximal domain. There are predicted N-linked glycosylation sites predicted at AA 65, 258, 272 and 286.

TIM-1 has been contemplated as a biomarker for kidney injury, for example U.S. Pat. No. 6,664,385 (Sanicola-Nadal et al.). However, there is no precedent for its use as a ligand for molecular imaging of selectins.

BRIEF DESCRIPTION OF THE DRAWINGS

FIG. 1 depicts the full-length amino acid sequence of the human TIM-1 protein. The extracellular domain is outlined with a dotted line.

DETAILED DESCRIPTION OF THE INVENTION

Figure 2:
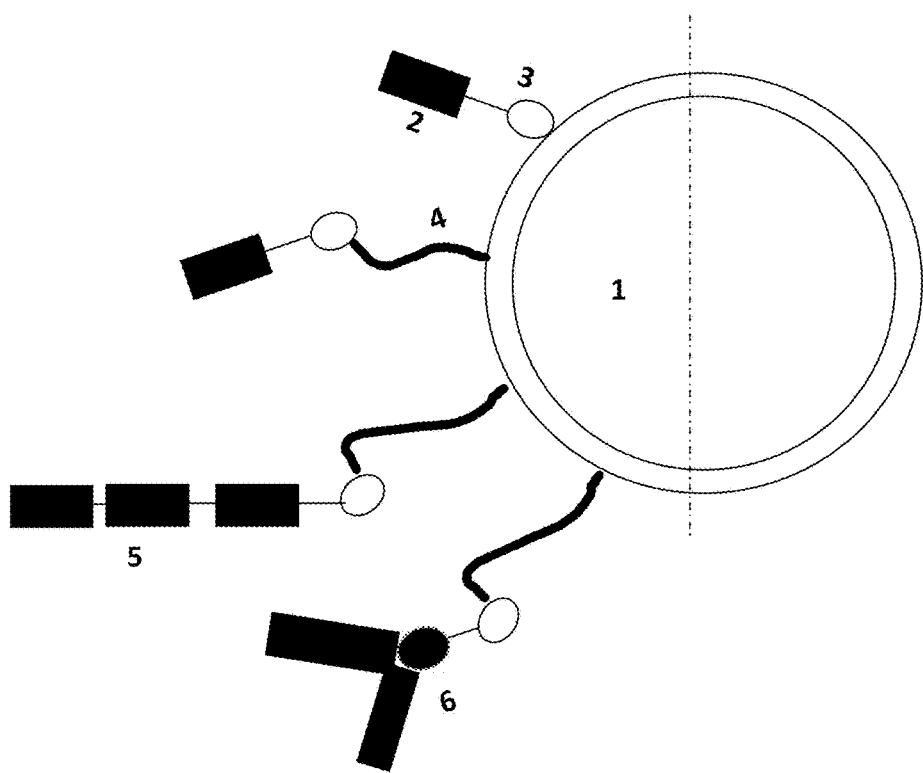
FIG. 2 depicts Molecular imaging agents comprising the extracellular domain of TIM-1, expressed as a fusion protein, as a targeting ligand. The contrast-producing substance (1) is attached to the TIM-1 fusion protein (2) by means of a chemical bond (3). In some embodiments, the contrast agent is attached to the TIM-1 fusion protein via an intervening polymer spacer (4). In some embodiments, the fusion protein exists as a multimer of 2 or more fragments of the extracellular domain of TIM-1 (5). In some embodiments, the fusion protein comprises the Fc domain of human IgG (6).

We have made the surprising discovery that the extracellular domain of the human glycoprotein TIM-1, when conjugated to a medical imaging contrast agent, enables specific binding of the contrast agent to selectins. Compositions comprising medical imaging contrast agents bearing the extracellular domain of TIM-1 as a targeting ligand for use in molecular imaging of selectins are herein disclosed. Use of the extracellular domain of TIM-1 as a ligand for achieving specific targeting to selectins of drug delivery vehicles is also contemplated.

Definitions

The abbreviations used herein have their conventional meaning within the chemical and biological arts.

As used herein, the term "microbubble" refers to a gas-encapsulated sphere stabilized by a biocompatible shell and which is suitable for use as an ultrasound contrast agent.

As used herein, the term "Targeting Ligand" or "ligand" refers to any material or substance that may promote targeting of tissues, cells, receptors, and/or marker groups in vitro or in vivo with the compositions of the present invention. The terms "target(s)", "targeted" and "targeting", as used herein, refer to the ability of targeting ligands and compositions containing them to bind with or be directed towards tissues, cells and/or receptors. The targeting ligand may be synthetic, semi-synthetic, or naturally-occurring. Materials or substances which may serve as targeting ligands include, for example, proteins, including antibodies, glycoproteins and lectins, peptides, polypeptides, saccharides, including mono- and polysaccharides, vitamins, steroids, steroid analogs, hormones, cofactors, bioactive agents, and genetic material, including nucleosides, nucleotides and polynucleotides.

As used herein, the term "selectin" refers to members of the selectin family of adhesion molecules, denoted by CD62P, CD62E, and CD62L.

As used herein, the term "recombinant fusion protein" refers to a fusion protein created by recombinant DNA technology, wherein said fusion protein comprises a Target-Binding Region and a Fusion Partner. In the context of the present invention, Target Binding Regions comprise SEQ ID NO: 2 and SEQ ID NO: 3. Fusion partners comprise affinity tags and conjugation residues, including Fc domains and His-tags, and cysteine-tags.

As used herein, the term "Active Substance" refers to a compound that is administered to a cell for the purpose of changing the phenotype or genotype of said cell. Exemplary active substances are plasmid DNA, siRNA, small molecule drugs, antibodies, and other therapeutic compounds.

As used herein, the term "Therapeutic Substance" refers to any therapeutic or prophylactic agent that may be used in the treatment (including the prevention, diagnosis, alleviation, or cure) of a malady, affliction, disease or injury in a patient or animal model. Therapeutically useful peptides, polypeptides and polynucleotides may be included within the meaning of the term therapeutic substance.

As used herein, the term "Cell" refers to an individual membrane-encapsulated unit of a living organism. Cells may comprise a unicellular organism, for example in the case of bacteria and yeast, or an individual unit of a larger organism.

As used herein, the term "Target Receptor" or "Molecular Target" refers to a molecular structure within a cell or on the surface of the cell that is generally characterized by the selective binding of a specific substance. Exemplary receptors include, for example, cell-surface receptors for peptide hormones, neurotransmitters, antigens, complement fragments, and immunoglobulins and cytoplasmic receptors for steroid hormones. An exemplary receptor is P-selectin (CD62P), which is associated with inflammation.

As used herein, the term "Animal Model" is defined as a non-human organism that is used in experimental research. Animal models include but are not limited to mice, rats, frogs, zebra fish, non-human primates, equines, canines, cats, swine, and insects.

As used herein, the term "Acoustic Activation" refers to the process of exciting an acoustically active agent, such as a microbubble, with incident acoustic energy. This process may stimulate the agent to produce acoustic energy, which may be detected and quantified by ultrasound imaging. Acoustic activation may further result in the rupture of the agent, whereby the encapsulated gas is released from the shell, and both shell and gas components are removed from the target site by biological means, including incident blood flow. While not intending to be bound by any particular theory of operation, microbubble rupture may occur by deflation of the gas core, explosion, cracking of the shell, or similar processes.

As used herein, the term "Isolation" refers to the act of isolating or completely separating one or more populations of cells from another population, and can refer to either Positive or Negative Selection.

As used herein, the term "Acoustically-Activated Delivery" refers to the process of delivering a compound, molecule, nucleic acid, protein, peptide, fluorophore, or reporter into a cell adjacent to a microbubble, wherein both microbubble and cell are treated with a low-frequency (1-10 MHz) high pressure (>50 kPa) acoustic field. While not intending to be bound by any particular theory of operation, acoustically-activated delivery transferring substances into the cell through transient pores or by active transport mechanisms induced by acoustic activation of an adjacent microbubble. Acoustically-activated delivery generally requires the violent destruction of the activated microbubble.

Expression as a Fusion Protein

One aspect of the invention comprises the extracellular portion of the TIM-1 protein (SEQ ID NO: 2) or SEQ ID NO: 3 expressed as a fusion protein prepared by recombinant DNA technology. Exemplary methods for generating recombinant proteins are discussed, for example, in Structural Genomic Consortium et al (2011). Fusion partners consistent with this invention should be selected so as to 1) facilitate conjugation of the fusion partner to the contrast agent, or 2) facilitate expression, purification or manufacturing of the recombinant protein. In a preferred embodiment, both 1 and 2 are achieved. It will be clear to one skilled in the art that a suitable fusion partner should not compromise or reduce the ability of the fusion protein to bind to selectins.

In one embodiment of the invention, the fusion partner comprises a terminal amino acid residue suitable for covalent bioconjugation. Exemplary amino acids for this purpose are cysteine and lysine. The presence of these terminal residues provides a facile means of conjugation of the fusion protein to the contrast agent. Such terminal modifications can be incorporated through so-called fusion tags, generally encompassing several (<30) amino acids. Terminal modifications suitable to the present invention are discussed by Wang and Chen (2008), hereby incorporated by reference.

In one preferred embodiment, the peptide tag comprises a terminal cysteine. Said cysteine may be incorporated on the N- or C-terminus of a short peptide sequence. Cysteine tags suitable for use in the present invention are disclosed by Backer et al (2006), hereby incorporated by reference.

In one embodiment, the fusion partner comprises the crystallizable fragment domain (Fc) of human IgG. In a particularly preferred embodiment, the Fc subclass has been selected, or the sequence modified, so as to minimize Fc effector functions (complement activation and recognition of the Fc domain by immune cells). This can be achieved, for example, by mutating the amino acids at positions 234 and 235 in human IgG1 Fc to alanine Other suitable strategies for reducing Fc effector functions are found in U.S. Pat. Nos. 5,264,821; 5,885,573, and 6,194,551.

The use of Fc domain as a fusion partner will be understood by one skilled in the art to facilitate large-scale manufacturing of the recombinant protein, owing to the high degree of efficiency with which Fc fusion proteins can be produced and purified.

In one embodiment, the fusion protein is expressed as a multimer. Without wishing to be bound by any particular theory, multimerization is expected to increase the efficiency with which the fusion protein binds to its selectin target. In one preferred embodiment, multimerization is achieved by selecting the Fc domain as the fusion partner, thereby achieving dimerization.

In one embodiment, the fusion partner comprises an oligomeric Histidine tag (His-tag). The presence of a His-tag is useful for efficiently purifying and concentrating the recombinant protein during manufacturing.

Cleavage and removal of the fusion tag after purification of the recombinant protein is consistent with the instant invention. For example, an N-terminal His-tag may be removed by the tomato etch virus protease, as described in Waugh et al (2011). It will be clear to one skilled in the art that placement of an amino acid suitable for bioconjugation proximal to the cleavage site is desirable for facilitating linking of the cleaved protein to the contrast agent.

Molecular Imaging Contrast Agents

One aspect of the invention comprises conjugating SEQ ID NO: 2 or SEQ ID NO: 3, expressed in the form of a fusion protein as described above, to a contrast-producing agent for the purpose of molecular imaging of selectins.

Medical imaging modalities useful in the context of the present invention include ultrasound (US), computed tomography (CT), magnetic resonance imaging (MRI), positron emission tomography (PET), single photon emission computed tomography (SPECT), X-ray imaging, fluorescence imaging, optical imaging, and photoacoustic imaging.

TABLE 1

Exemplary contrast agents suitable for use in the current invention.

| Modality | Contrast-Producing Agent |
| --- | --- |
| Ultrasound | Microbubble, acoustically active liposome |
| CT/X-Ray | Gold nanoparticles, iodinated nanoparticles, |
| MRI | Hyperpolarized neon/xenon/helium, gadolinium, iron oxide |
| PET | $^{18}F$, $^{11}C$ |
| SPECT | $^{99m}Tc$, $^{123}I$, $^{111}In$ |
| Fluorescence Imaging | Cy7, microbubble comprising DiR, IRDye800CW, GFP, AlexaFluor 647 |

TABLE 1-continued

Exemplary contrast agents suitable for use in the current invention.

| Modality | Contrast-Producing Agent |
| --- | --- |
| Photoacoustic Imaging | Carbon single-wall nanotubes (SWINT), indocyanine green, gold nanoparticles, zinc phthalocyanine |

Exemplary contrast-producing agents include radionuclides such as 99mTc and 123I, positron-emitting isotopes such as 18F or 64Cu, fluorochromes such as Alexafluor- or Cy-dyes, substances with high magnetic susceptibility such as iron and gadolinium, echogenic particles such as microbubbles or echogenic liposomes, and combinations thereof.

In a preferred embodiment, the medical imaging modality is ultrasound imaging and the contrast-producing agent is a gas-encapsulated microbubble.

Microbubble Gas Considerations

Microbubbles can be prepared from a variety of gases, including air, nitrogen, argon, sulfur hexafluoride, perfluoroethane, perfluoropropanes, perfluorobutanes, perfluorocyclobutanes, perfluoropentanes, perfluorocyclopentanes, perfluoro methylcyclobutanes, perfluorohexanes, perfluorocyclohexanes, perfluoro methyl cyclopentanes, perfluoro dimethyl cyclopentanes, perfluoro heptanes, perfluoro cycloheptanes, perfluoro cycloheptanes, perfluoromethyl cyclohexanes, perfluoro dimethyl cyclopentanes, perfluoro trimethyl cyclobutanes perfluoro triethylaminesperfluoropropane, perfluorobutane and similar, or a mixture thereof. It will be understood to one skilled in the art that selection of the encapsulated gas, or mixture thereof, will be selected so as to achieve the microbubble size distribution and in vivo lifetime suitable for the intended application.

In one embodiment perfluorocarbon gasses, specifically decafluorobutane ($C_4F_{10}$) and octofluoropropane ($C_3F_8$) are used. In one embodiment, said perfluorocarbon gasses are admixed with nitrogen or air at a ratio of 40:60 (perfluorocarbon gas:nitrogen or air).

Microbubble Shell Considerations

The gas core of a microbubble is stabilized with a thin, preferably monolayer, shell of a biocompatible substance. Exemplary shell materials include lipids, proteins, carbohydrates, and polymers. Such microbubbles can additionally incorporate a hydrophilic polymer such as polyethyleneglycol (PEG), PVP, or polyglycerol. These substances can act as emulsifiers, increase stability, and assure low non-specific retention of the microbubble to other materials and surfaces.

In a preferred embodiment, the shell comprises monolayer of lipids. In a most preferred embodiment, the shell comprises a mixture of three or more lipid species: a primary shell forming lipid, a secondary shell forming lipid, and an anchor.

The primary shell forming lipid forms the majority of the shell. It is desirable that this component exhibit no net charge. Exemplary lipids for use as primary shell forming lipids include phosphatidylcholines, in particular disteroylphosphatidylcholine (C18:0), dipalmitoylphosphatidylcholine (C16:0). The primary shell forming lipid composes 50-98% of the microbubble shell (by moles).

The secondary shell forming lipid comprises an amphipathic species bearing a water-soluble polymer chain. In a preferred embodiment, the secondary shell forming lipid comprises a chain of poly(ethyleneglycol) (PEG) on a hydrophobic anchor. Exemplary species include PEG-lipids, and PEG-fatty acids. Most preferred species are disteroylphosphatidylethanolamine (C18:0)-PEG and dipalmitoylethanolamine (C16:0)-PEG, in which the PEG chain grafted to the lipid headgroup is of molecular weight between 500-5,000. The secondary shell forming lipid composes 1-49% of the microbubble shell (by moles).

The anchor serves to bind the targeting ligand to the microbubble shell. Anchors suitable for use in the instant invention comprise a hydrophobic portion, providing for insertion into the lipid shell; a hydrophilic portion, which is in contact with the liquid media; and a conjugation residue, providing for linkage of the targeting ligand to the anchor. The anchor may be modular, comprising separate hydrophobic, hydrophilic, and conjugation portions, or may comprise a single entity. In a preferred embodiment, the hydrophilic portion comprises a polymer chain and acts as a spacer between the targeting ligand and the microbubble body. Representative anchors suitable for use in the instant invention are disclosed, for example by Klibanov (U.S. Pat. No. 6,245,318). Exemplary anchors for use in this invention include distearoylphosphatidylethanolamine-PEG, in which the PEG is of molecular weight 2000-5000. The distal tip of the PEG molecule comprises a residue suitable for conjugation of the targeting ligand (discussed below). The anchor composes 0.1-5% of the microbubble shell (by moles).

Conjugation residues comprising biocompatible conjugation chemistries are preferred. Suitable residues are disclosed, for example, by Klibanov (U.S. Pat. No. 6,245,318) and Unger (U.S. Pat. No. 6,139,819). Maleimide, sulfhydryl, amine, and carboxyl functionalities are preferred. In a preferred embodiment, the targeting ligand comprises a sulfhydryl and the anchor comprises a maleimide group.

The size of the microbubbles should be consistent with intravascular use and contrast ultrasound imaging. In general, microbubbles of diameter between 0.5-5.0 um exhibit favorable intravascular rheology and are echogenic at most diagnostic imaging frequencies. It will be clear to one skilled in the art that the size distribution of the microbubble preparation may be selected so as to achieve a favorable imaging response for the desired application. For example, the formulation may be enriched in microbubbles of a restricted size range in order to optimize the performance for a specific diagnostic imaging setting or frequency. Methods for selectively enriching microbubbles by diameter are disclosed, for example, in Feshitan et al. (2009).

In a preferred embodiment, the majority of microbubbles in the formulation possess a diameter of between 1-3 μm.

In some embodiments, the microbubble composition further comprises a fluorophore.

Applications in Molecular Imaging and Therapy

One aspect of the invention comprises a method of imaging selectin expression in a tissue of a patient, said method comprising the steps of 1) administering to a subject a medical imaging contrast agent wherein SEQ ID NO: 2 or SEQ ID NO: 3 expressed as a fusion protein is conjugated to the contrast-producing agent, 2) allowing sufficient time for the contrast agent to accumulate and for free agent to clear the target tissue, and 3) imaging the target tissue with the relevant imaging modality.

In one embodiment, the patient is an experimental animal used as a model of human disease.

In one embodiment, the patient is a human.

In one embodiment, the imaging method is intended to render a diagnosis based on the presence or absence of selectin expression within the imaged tissue.

In one embodiment, the molecular target is P-selectin. In another embodiment, the molecular target is E-selectin. In yet another embodiment, the molecular target is both P- and E-selectin.

In one embodiment, the molecular target is expressed on vascular endothelium. In another embodiment, the molecular target is expressed on platelets. In yet another embodiment, the molecular target is expressed on cell-derived microparticles bound to the vascular endothelium.

In one embodiment, the targeted tissue is an internal organ, including the heart, kidney, bowel, liver, spleen, pancreas, lungs, stomach, or brain. In another embodiment, the targeted tissue is skeletal muscle. In another embodiment, the targeted tissue is adipose tissue. In another embodiment, the targeted tissue is vascular endothelium lining the arteries. In another embodiment, the targeted tissue is arterial vasa vasorum. In another embodiment, the targeted tissue is the testicle.

In one embodiment, the method is used to diagnose post-ischemic injury.

In a preferred embodiment, the contrast agent comprises a microbubble, and the imaging modality is ultrasound.

In one embodiment of the invention, said imaging method depicts the presence or absence of selectins in the imaged tissue. For example, the method may be used to render a binary diagnostic decision based on the presence or absence of contrast enhancement above a pre-determined threshold. In this case, presence of contrast enhancement would indicate the presence of selectin expression within the imaged tissue.

In another embodiment of the invention, said imaging method depicts the spatial location of selectin expression in the imaged tissue. For example, the location of diffuse lesions comprising activated platelets may be deduced by imaging the length of the proximal femoral artery and noting localized regions of contrast enhancement.

In another embodiment of the invention, said imaging method depicts the relative amount of selectin expression in the imaged tissue. For example, identification of post-ischemic regions of the myocardium by visualization of regions of selectin up-regulation or expression within the myocardium is possible with the instant invention.

In one embodiment, the amount of selectin present in the region of interest is computed from the provided image, thereby comprising a quantitative measurement.

In one embodiment, the amount of selectin present in one region relative to another region is computed, thereby comprising a relative measurement. For example, in the context of cardiac imaging the contrast signal within the left or right ventricle can be used to normalize enhancement within various regions of the myocardium. This provides a method for computing the relative degree of targeted contrast enhancement within the myocardium.

In one embodiment, more than one imaging modality is employed.

Another aspect of the invention entails using SEQ ID NO: 2 or SEQ ID NO: 3, expressed as a fusion protein, as a ligand to mediate binding of a targeted drug delivery vehicle to selectin. Exemplary drug delivery vehicles include liposomes, micelles, polymers, stabilized emulsions, chelates, microbubbles, nanotubes, and combinations thereof.

In one embodiment, the drug delivery vehicle comprises a microbubble, and delivery of the drug is mediated by sonoporation.

In one embodiment, the drug delivery vehicle is administered intravenously, intraperitoneally, intrathecally, subcutaneously, or intramuscularly.

Another aspect of the invention comprises a method of treating a subject with ischemic injury that induces expression of P-selectin, E-selectin or both, the method comprising administering to a subject a therapeutically effective amount of a compound contained in a drug delivery vehicle comprising the disclosed targeting ligand.

EXAMPLES

The following examples are provided by way of illustration only and not by way of limitation. Those of skill will readily recognize a variety of noncritical parameters that could be changed or modified to yield essentially similar results.

Example 1

Adhesion of Recombinant Protein to Human P-Selectin

The ability of various recombinant forms of TIM-1 to bind human P-selectin was assessed in an in vitro affinity assay. Recombinant human P-selectin (R&D Systems) was incubated on medium-binding 96 well plates (Greiner Bio-One) overnight at 4 deg C. Wells were blocked for 2 hours at room temperature with BSA in PBS. Recombinant protein samples were then added at the concentrations specified in Table 2 and incubated for 1 hour. Plates were washed, then incubated with an anti-human Fc-biotin secondary (eBioscience) or an anti-His-biotin secondary (for sample D) for 1 hour at room temperature. Plates were washed, then detected with HRP-conjugated streptavidin (Rockland) for 1 hour at room temperature. Plates were subsequently developed with TMB solution, and optical absorbance read in a plate reader at 450 nm. As a positive control, recombinant human PSGL-1 was used. As a negative control, the anti-Fc secondary alone was used. As a negative control, an irrelevant IgG molecule was used.

TABLE 2

Identity and concentration of recombinant proteins used in P-selectin affinity assay.

| Sample | Description | Expressed In | Concentration |
|---|---|---|---|
| A | Recombinant human PSGL-1 | CHO | 50 ug/mL |
| B | SEQ ID NO: 3 with N-terminal human IgG1 Fc | CHO | 28.1 ug/mL |
| C | SEQ ID NO: 2 with N-terminal human IgG1 Fc and C-terminal His tag | HEK293 | 33.2 ug/mL |
| D | SEQ ID NO: 2 with C-terminal His tag | HEK293 | 23.0 ug/mL |
| E | SEQ ID NO: 2 with N-terminal His tag | HEK293 | 25.5 ug/mL |

Figure 3:
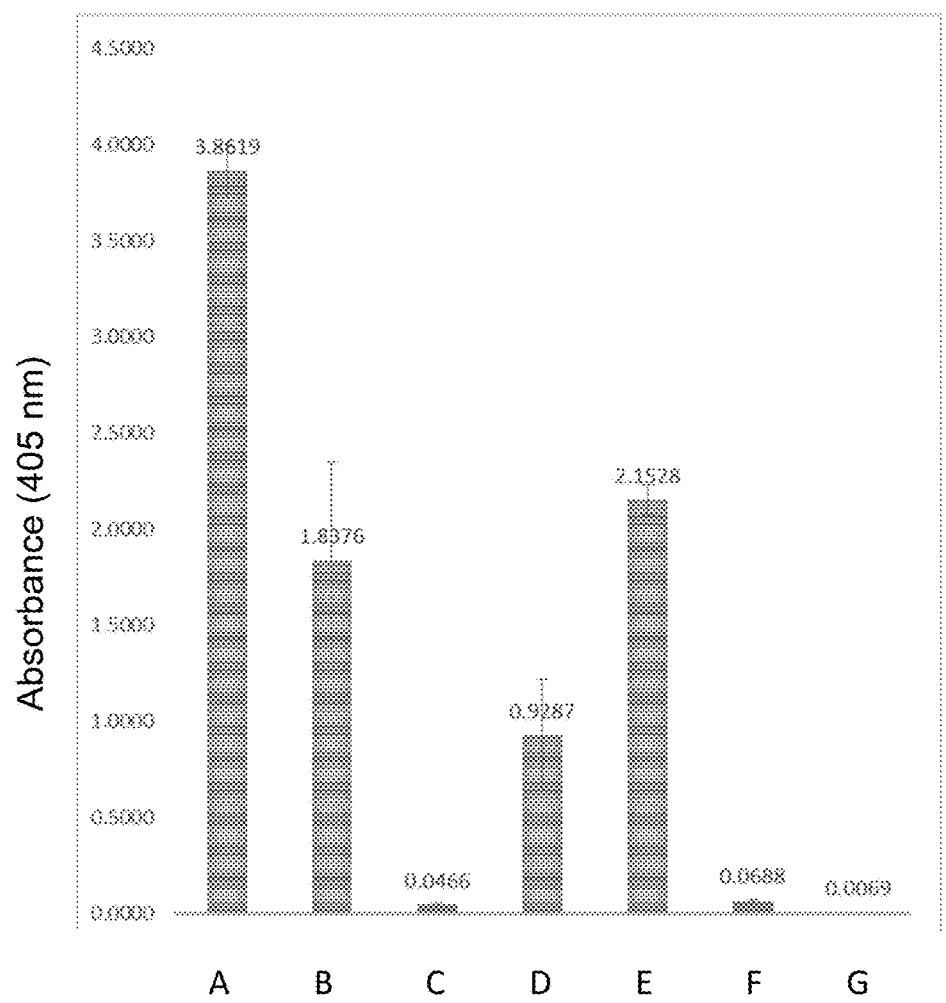
FIG. 3 depicts the results of affinity assay on recombinant human P-selectin (rhP-sel). Samples A-G were incubated on wells coated with rhP-sel, then detected with an HRP-conjugated secondary. Data are expressed in optical absorbance units. (A) is the recombinant human PSGL-1 (CD162). (B) is the recombinant protein comprising SEQ ID NO: 3 with a N-terminal human IgG1 Fc. (C) is the recombinant protein comprising SEQ ID NO: 2 with a N-terminal human IgG Fc and a C-terminal His tag. (D) is the recombinant protein comprising SEQ ID NO: 2 with a C-terminal His tag. (E) is the recombinant protein comprising SEQ ID NO: 2 with a N-terminal His tag. (F) is a control (detection reagent only). (G) is a control (irrelevant IgG protein).

Negligible binding of the negative control conditions was observed (<0.1 absorbance units, AU). Appreciable binding (>1 AU) was observed for Samples A,B,D, and E. Negligible binding of sample C was observed, suggesting that modification of both the N- and C-termini are incompatible with P-selectin binding (FIG. 3).

Example 2

Preparation of Encapsulated Microbubble Contrast Agents

Microbubbles comprising a decafluorocarbon gas core encapsulated by a two shell-forming surfactant shell were prepared as follows: 100 mg of the primary shell-forming lipid disteroylphosphatidylcholine (Avanti) and 65 mg of the seconds shell-forming lipid disteroylphosphatidylethanolamine-PEG(2000) (DSPE-mPEG(2000)) (Avanti) were solubilized by low-power sonication (20 minutes at 9 W; CP-505 sonicator, Cole-Parmer) in 0.9% injection grade NaCl (normal saline; Baxter). The mixture was heated to 70° C., and microbubbles formed by high-power sonication (30 s at 40 W) while sparging decafluorobutane gas (Fluoromed). This procedure resulted in the formation of a polydisperse, right-skewed dispersion of lipid-stabilized microbubbles of decafluorobutane, at a concentration of ~4E9 per mL. The resulting microbubble dispersion was then allowed to cool to room temperature. Shell forming materials not incorporated into microbubbles were removed by centrifuging the dispersion for 10 minutes at 1000×G, 15° C. (Allegra 6R bucket centrifuge; Beckman-Coulter) in a 100 mL sealed glass vial with a decafluorobutane gas headspace and collecting the infranatant with a thin needle. Microbubbles were then re-suspended at a concentration of 4E9 per mL in a buffer containing of 300 g/L glycerin, 300 g/L propylene glycol in normal saline, pH 5-6.5 (saline/glycerin/propylene glycol buffer).

Example 3

Preparation of Targetable Microbubble Contrast Agents

Microbubbles suitable for conjugation of a targeting ligand were prepared by incorporating into the blend described in Example 2 an anchor molecule and synthesizing as in Example 2. Here, microbubbles bearing the reactive group 2-pyridyl disulfide (PDP) were prepared as follows: 100 mg of disteroylphosphatidylcholine (primary shell-forming lipid), 65 mg DSPE-mPEG(2000) (secondary shell-forming lipid), and 5 mg of PDP-PEG(2000)-disteroylphosphatidylethanolamine (DSPE-PEG(2k)-PDP; Avanti) (anchor) were added to 50 mL of sterile normal saline and sonicated to clarity using a probe-type sonicator. Microbubbles were formed by sonicating in the presence of octofluoropropane gas, and washed as in Example 2. This procedure resulted in the formation of a polydisperse dispersion of lipid-stabilized microbubbles of decafluorobutane, at a concentration of ~4E9 per mL. Microbubbles were re-suspended at a surface area concentration of 2E11 μm²/mL in Dulbecco's phosphate buffered solution (DPBS) containing 300 mg/mL of glycerin and 300 mg/mL of propylene glycol, pH 7.4 (DPBS/glycerin/propylene glycol buffer). Microbubbles were stored in sealed glass vials under a headspace of decafluorobutane gas for up to 6 months.

In a separate experiment, similar microbubbles were prepared in which the second shell-forming lipid comprised a different species of PEG. Fifty mg of DSPE-PEG(1k) (second shell-forming lipid), 100 mg of DSPC (primary shell-forming lipid), and 5 mg of DSPE-PEG(2k)-PDP (anchor) was added to 50 mL of normal saline and sonicated to clarity. Microbubbles were prepared as described above. This procedure resulted in the formation of a polydisperse dispersion of lipid-stabilized microbubbles of decafluorobutane, at a concentration of ~4E9 per mL, number-weighted mean diameter of 1.4 μm and >90% between 1-2 μm. These microbubbles were washed and stored as described above.

Incorporation of the PDP residue enables conjugation of a targeting ligand to the microbubble surface via sulfhydryl-directed conjugation chemistry. Various other ligand conjugation chemistries can be readily used by substituting for the DSPE-PEG(2000)-PDP component. Ligands can be immobilized via thioether linkage by incorporating 5 mg/mL of maleimide-PEG(2000)-DSPE. Other reactive groups suitable for ligand conjugation include amino, azide, carboxylic acid, succinyl functional groups.

It will be obvious to one skilled in the art that the density of the reactive group within the microbubble shell can be modulated by the mass fraction of the reactive group added during the synthesis step, and that the density of the targeting ligand can be optimized so as to ensure desirable pharmokinetics, safety, and target binding ability in vivo.

Example 4

Conjugation of Recombinant Fusion Protein to Microbubble

A human IgG1 Fc recombinant protein comprising SEQ ID NO: 3 as the fusion partner was conjugated to the surface of lipid microbubbles as follows.

0.1 mg of recombinant protein was reacted with the amine-sulfhydryl heterobifunctional crosslinker SMCC (Pierce) for 30 minutes, then purified by size exclusion column.

PDP-bearing microbubbles were prepared for as in Example 3. The microbubbles were incubated with 2 mM tris (2-carboxyethyl) phosphine-based reducing agent (TCEP; Pierce) to convert the stable PDP residue to the reactive sulfhydryl form. Reducing agent and reduction bi-product was removed by washing the microbubbles three times at 15 deg C. in DPBS/glycerin/propylene glycol buffer. Microbubbles were concentrated to 2E11 $\mu m^2$/mL.

Figure 4:
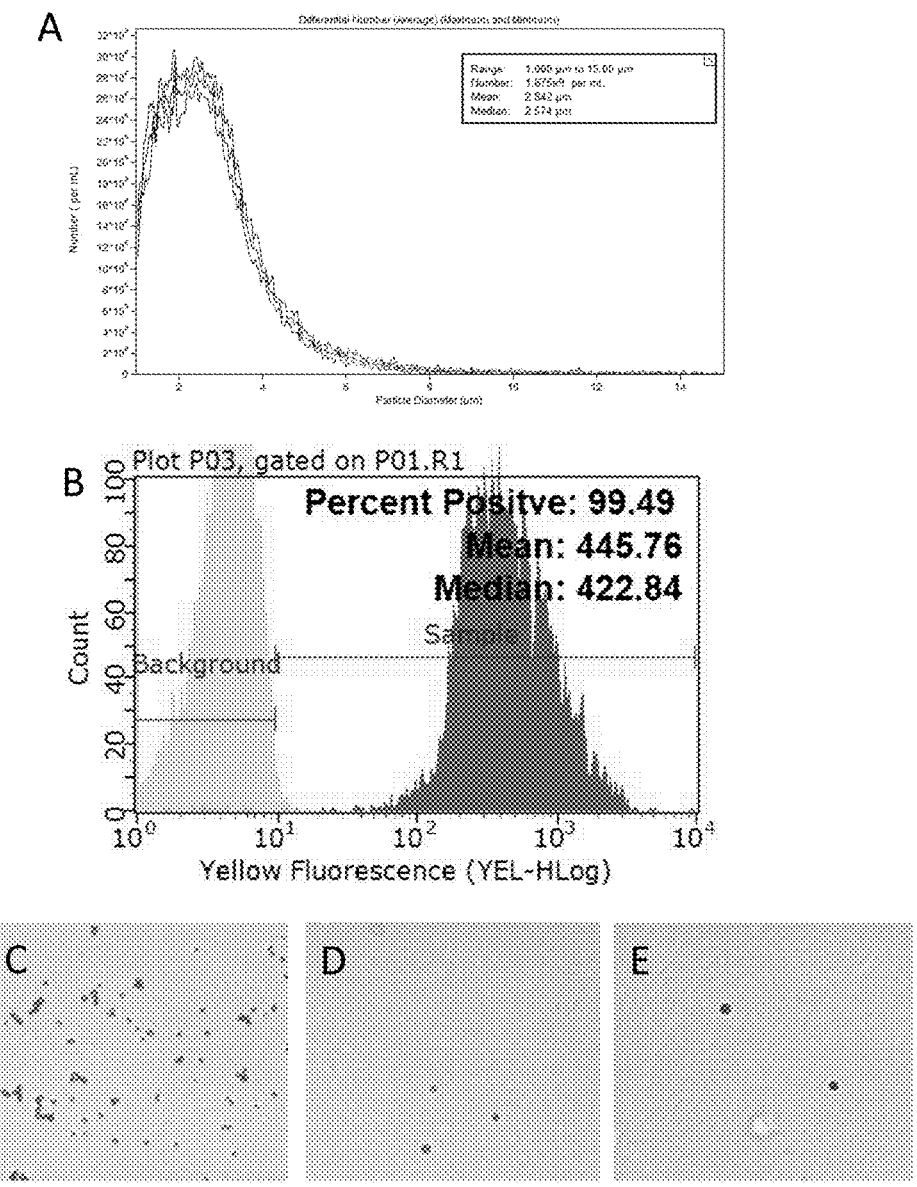
FIG. 4: Preparation and evaluation of microbubble-based molecular imaging agents comprising the extracellular domain of human Tim-1 (SEQ ID NO: 2) fused to a human IgG1 Fc domain. (A) electrozone (Coulter) analysis demonstrated a size distribution amenable for use as an ultrasound contrast agent. (B) Staining microbubbles with a FITC-conjugated antibody against human Fc and analyzing by flow cytometry revealed the presence of the TIM-1.Fc recombinant protein on the microbubble surface. Background is identical microbubbles in which the reactive group had been blocked with IAM. (C) static adhesion of TIM-1.Fc microbubbles on a surface of recombinant human P-selectin demonstrated substantial microbubble binding, while (D) negligible binding was observed on a blocked substrate (casein). (E) Microbubbles not bearing the TIM-1.Fc fusion protein exhibited negligible adhesion on human P-selectin.
Figure 5:
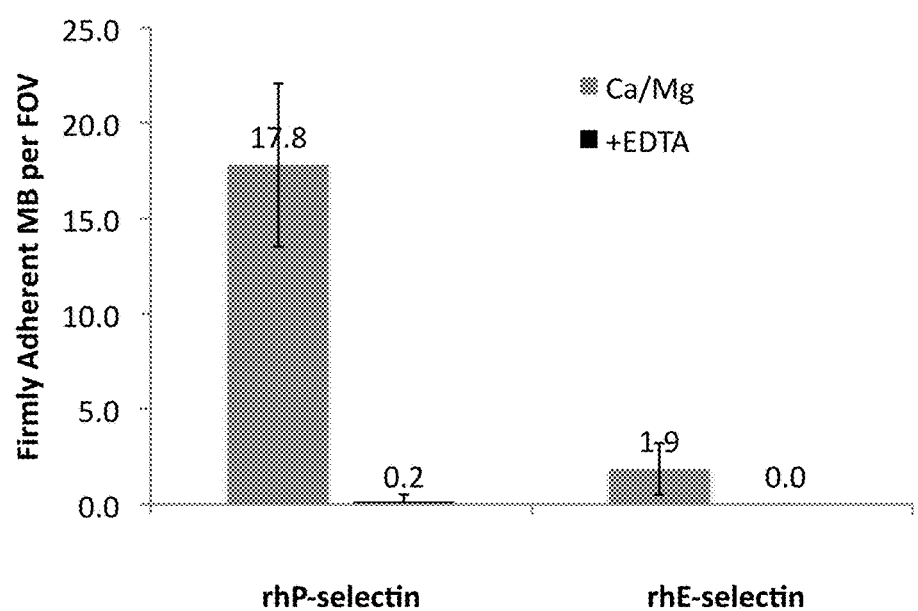
FIG. 5: Functional adhesion of microbubbles bearing SEQ ID NO: 2 dimerized on a human IgG1 Fc to human selectins. Microbubbles were infused through a flow chamber coated with recombinant human P- or E-selectin at a wall shear stress of 4.2 dyne/cm2. Firmly adherent microbubbles were counted in 20 random fields of view. As a negative control, the experiment was repeated in a buffer containing 5 mM EDTA. Adhesion was observed on both selectins, although at a higher degree for P-selectin. Negligable to no adhesion was observed in the presence of EDTA.
Figure 6:
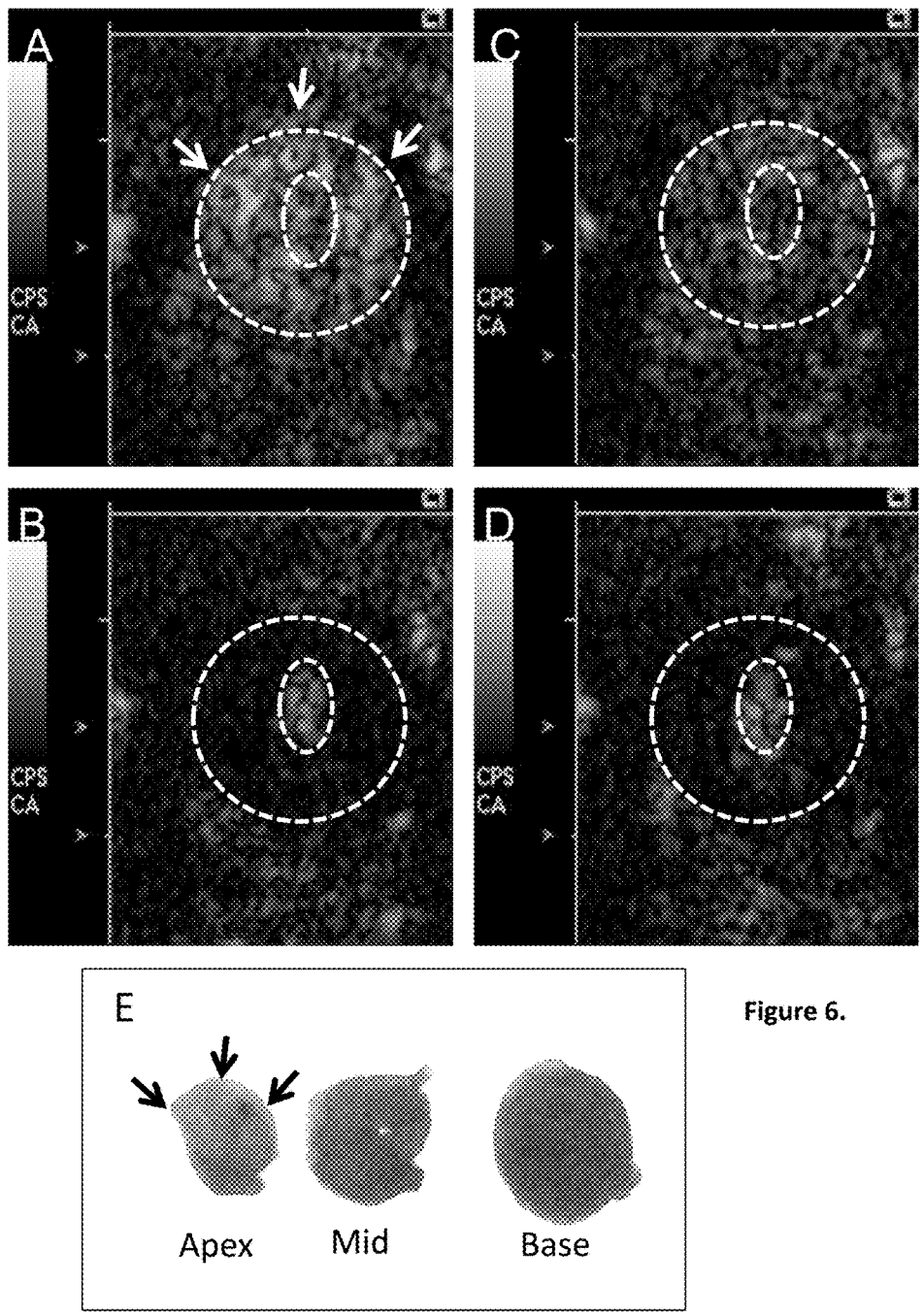
FIG. 6 depicts molecular imaging of ischemic injury in mouse myocardium. Mice were anesthetized and ventilated on medical air. The left anterior descending artery was ligated for 10 minutes, then the ligature was released and the myocardium allowed to re-perfuse. 30 minutes after ligature release, mice were administered 1E6 microbubbles, and the contrast signal within the myocardium was visualized at 10 minutes in the short axis using contrast ultrasound imaging (MI=0.20, 8.0 MHz, using contrast pulse sequencing on a Siemens Sequoia). (A) microbubbles comprising SEQ ID NO: 3 expressed as a fusion protein with human IgG Fc exhibited a significant contrast signal (arrows). (B) Negligible contrast signal was observed 5 s after administration of a destructive burst (MI=1.9, 1.0s duration), suggesting that the signal observed in (A) was due to microbubbles retained within the tissue and not circulating. (C) Significantly less contrast enhancement was observed for microbubbles bearing a control ligand (Streptavidin), and the same absence of circulating microbubbles was observed (D). (E) Ex vivo perfusion staining with pthalocyanine blue (5%, 200 uL administered by LV puncture prior to sacrifice) revealed a significant apical perfusion defect (light colored tissue depicting absence of perfusate, depicted by arrows) within the region where significant contrast signal was observed in (A).
Figure 7:
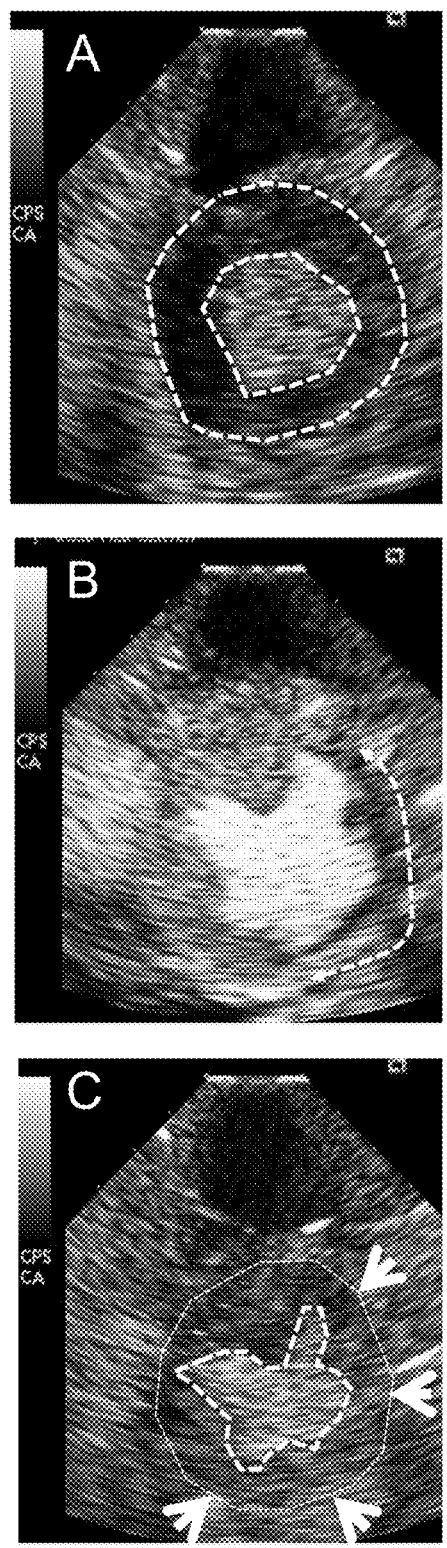
FIG. 7 depicts molecular imaging in a canine model of acute coronary syndrome. An adult male beagle was anesthetized and ventilated on oxygen. The thoracic cavity was opened and the heart exposed for ultrasound imaging. 8E8 targeted microbubbles (targeting ligand consisting of an Fc fusion of SEQ ID NO: 2) in 0.2 mL were administered intravenously followed by a 4 mL flush. The heart was imaged in the short axis. (A) Negligible contrast signal was observed within the myocardium (myocardium is delineated by dotted lines) 4 minutes after microbubble infusion (2.0 MHz, MI=0.19, CPS with Siemens Sequoia). The left anterior descending artery was then ligated. (B) Perfusion imaging with a non-targeted microbubble contrast agent (Targestar P) revealed a significant perfusion defect (dotted line). The ligature was released after 10 minutes of ischemia, and the myocardium allowed to re-perfuse for 30 minutes. Full re-perfusion was verified by perfusion imaging (not shown). (C) The targeted microbubble preparation was then administered as in (A). Significant contrast enhancement was observed within the myocardium corresponding to the previously ischemic zone (arrows).

The size distribution of targeted microbubbles was assessed by electrozone sensing (Coulter), and revealed a polydisperse population with a median diameter of 2.5 $\mu m$ and few (<1%) microbubbles of diameter greater than 8 $\mu m$ (FIG. 4A).

The presence of the recombinant protein was verified by flow cytometry, microbubbles were incubated for 10 minutes with a FITC-conjugated anti-human Fc antibody, and fluorescence on each microbubble was assessed by flow cytometry. Relative to control microbubbles in which the sulfhydryls had been blocked with IAM, microbubbles conjugated with the recombinant protein were 10-100 fold brighter (FIG. 4B).

It will be clear to one skilled in the art that the specific conjugation chemistry used to attach the TIM-1 protein to the microbubble can be tailored to the specific form of the TIM-1 protein. For example, TIM-1 is prepared such that the extracellular domain comprises a c-terminal glycine. TIM-1 is reacted with pyridoxyl phosphate and subsequently conjugated to hydrazide-functionalized microbubble via hydrazone bonds.

Example 5

Specific Binding of Targeted Microbubble Imaging Agent to Human P-selectin In Vitro Microbubbles bearing the recombinant protein were prepared as in Example 4. Binding of these microbubbles to human P-selectin is assessed in a static adhesion assay as follows: 50 ng of recombinant human P-selectin (Fc chimera; R&D Systems) was incubated on a 35 mm polystyrene culture dish overnight at 4 deg C. The dish was rinsed three times with 0.05% TWEEN, and incubated for 1 hour at room temperature with casein to block non-specific adhesion. As a negative control, some dishes were incubated with casein alone (no P-selectin). Microbubbles were diluted to 1E9 and 20 $\mu L$ was added to the dish. The dish was inverted for 2 minutes to allow the microbubbles to contact the surface. The dish was then gently rinsed with DPBS to remove un-bound microbubbles. Microbubbles bound to the dish were visualized by transillumination microscopy (20× objective).

Numerous (>20 per field of view) microbubbles bearing the recombinant protein (prepared as in Example 4) were observed on dishes coated with P-selectin (FIG. 4C). Negligible adhesion was observed on control dishes incubated with casein alone (FIG. 4D). In a separate experiment, microbubbles bearing IAM alone (no protein) were prepared as in Example 4. Negligible adhesion of these microbubbles was observed on P-selectin dishes (FIG. 4E).

Example 6

Functional Adhesion of Targeted Microbubble Imaging Agent to human P-selectin In Vitro Functional adhesion of targeted microbubbles to human selectins under dynamic flow was assessed as follows. Flow chambers (Microslide III-0.1; IBIDI) were incubated with 50 $\mu g$/mL of recombinant human P-selectin or recombinant human E-selectin (R&D Systems) overnight at 4 degrees C. Chambers were subsequently washed three times with DPBS and incubated for 1 hour at room temperature with casein to block non-specific adhesion. Targeted microbubbles prepared as in Example 4 were diluted to 5E6 per mL in PBS containing 2.0 mM Ca++ and 2.0 mM Mg++ and infused through the flow chamber at a shear stress of 4.3 dyne/cm$^2$ using a withdrawal syringe pump. Microbubble adhesion to the dish surface is observed from above using an upright microscope, and microscopic data are recorded using a digital video camera. Adherent microbubbles within 20 fields of view are counted after 5 minutes of infusion. As a negative control, microbubbles were dispersed in PBS containing 5 mM EDTA and perfused through flow chambers as described above.

Targeted microbubbles exhibited negligible adhesion to P- or E-selectin when perfused in EDTA (0.2 and 0 microbubbles per field of view, respectively). In the presence of divalent cations (Ca/Mg), microbubble adhesion was observed to both P- and E-selectin (17.8 and 1.9 microbubbles per field of view, respectively). Greater adhesion was observed on P-selectin relative to E-selectin. This experiment confirms the ability of microbubbles bearing the recombinant protein to bind to human endothelial selectins under physiological shear flow.

Example 7

Use of Targeted Microbubbles for Detecting the Presence Post-Ischemic Cardiac Injury P- and E-selectin are up-regulated on the vascular endothelium within myocardium during ischemia-reperfusion. The ability of targeted microbubbles to detect the presence of ischemic injury was evaluated in this experiment. A 16 week male c57/B16 mouse was anesthetized and maintained on isoflurane in medical air via a ventilator. The chest cavity was surgically opened and the heart exposed. A surgical suture was looped around the left anterior descending coronary artery, and reversibly tightened. Contrast ultrasound imaging using a perfusion imaging agent (Targestar- P) revealed a significant apical perfusion defect. After 10 minutes, the ligation was released and the myocardium allowed to re-perfuse for 30 minutes. The mouse was administered 1E6 targeted microbubbles (prepared as in Example 4) in 20 µL by retro-orbital injection. Wash-in of the contrast agent through the entire myocardium, including the previously ischemic regions, was visualized over 10 minutes by non-destructive contrast ultrasound imaging on a Siemens Sequoia (8.0 MHz, MI=0.20, CPS). After 10 minutes, a destructive ultrasound pulse was administered (8.0 MHz, MI=1.9), and myocardium was imaged for an additional 5 seconds. The mouse was administered a control microbubble formulation comprising an irrelevant protein ligand, and the imaging sequence repeated. Following imaging, the suture was re-ligated and the mouse administered ~200 µL of 5% pthalocyanine blue dye in order to demarcate the perfusion defect. The heart was excised, flushed, and sliced into three short axis planes for visualization of dye uptake. The experiment was repeated in n=2 mice.

A significant contrast signal was observed throughout the myocardium or the targeted microbubble. Five seconds after destruction, negligible contrast signal was observed in the myocardium, indicating that the signal at 10 minutes was due to bound, not circulating, microbubbles. Significantly lower contrast enhancement was observed for the control microbubble. Pthalocyanine blue staining revealed the presence of a significant perfusion defect at the apical-anterior myocardium.

Example 8

Use of Targeted Contrast Agent for Evaluating Acute Coronary Syndrome by Ultrasound Molecular Imaging The ability of targeted microbubbles to detect acute coronary syndrome (ACS) was evaluated in a canine model. An adult male beagle was anesthetized and maintained on sevoflurane in oxygen by ventilator. The chest cavity was surgically opened and the heart suspended in a pericardial cradle. A bolus of 4E8 targeted microbubbles (prepared as in Example 4) was administered intravenously through a femoral cannula. The contrast signal within the myocardium was evaluated 4 minutes after microbubble administration by non-destructive ultrasound imaging on a Siemens Sequoia (2.0 MHz, MI=0.31, CPS). Negligible contrast enhancement was observed at any location within the myocardium.

The left anterior descending coronary artery was then reversibly ligated, and the location and extent of ischemia was imaged by perfusion ultrasound imaging. A perfusion defect encompassing approximately 40% of the left ventricular wall was observed. After 10 minutes, the ligation was released and the myocardium allowed to re-perfuse for 30 minutes. Complete re-perfusion of all segments of the myocardium (including previously ischemic) was verified by perfusion imaging. Targeted microbubbles (prepared as in Example 4) were administered after 30 minutes of re-perfusion, and wash-in through the entire myocardium was observed by non-destructive ultrasound imaging. At 5 minutes, a significant contrast signal was observed in the region of myocardium that had been previously ischemic. The intensity of this contrast enhancement was significantly greater than that observed under the baseline condition (before ligation).

Example 9

Use of Targeted Contrast Agent for Detecting Acute Inflammation

P-selectin up-regulation is found in the context of acute inflammation in many tissues, including skeletal muscle. The ability of targeted microbubbles to detect acute inflammation was assessed in mouse hindleg. A healthy C57/B16 mouse was anesthetized and maintained on isoflurane in medical air. The animal was administered 5E6 or 1E7 targeted microbubbles (prepared as in Example 4), and the left proximal hindlimb was imaged by non-destructive ultrasound imaging on a Siemens Sequoia (8.0 MHz, MI=0.25, CPS). Ten minutes after microbubble injection, a destructive ultrasound pulse (MI=1.9, 1.0 s duration) was administered, and the contrast signal imaged over an additional 10 seconds. Negligible contrast enhancement was observed at either dose, demonstrating the absence of microbubble binding to resting skeletal muscle.

In a separate experiment, a healthy mouse was administered 500 ng of recombinant murine TNF-alpha (R&D Systems) in 20 µL subcutaneously into the left foodpad in order to induce an inflammatory response. Two hours after cytokine administration, the mouse was anesthetized and imaged with 5E6 or 1E7 targeted microbubbles. The mouse was also administered control microbubbles comprising an irrelevant protein (streptavidin), or microbubbles in which no ligand had been conjugated. 30 seconds of destructive ultrasound imaging was performed between doses.

Significant contrast enhancement was observed for targeted microbubbles at both doses. Enhancement was observed for control microbubbles bearing irrelevant protein, although this was significantly lower than that of the targeted microbubbles. Microbubbles bearing no protein ligand exhibited a significant contrast signal; 10 seconds after application of a destructive burst the signal intensity was largely unchanged, indicating that the contrast enhancement for this microbubble was due to circulating (not bound) microbubbles.

Example 10

Use of Targeted Contrast Agent for Evaluating Acute Coronary Syndrome by Molecular Imaging Selectins are molecular markers of post-ischemic injury in the myocardium, and molecular imaging of selectin expression can be used to diagnose the presence of acute coronary syndrome in human patients. Targeted microbubbles bearing the recombinant protein described in this application are administered intravenously to a patient. The contrast signal is continuously observed and recorded by ultrasound imaging over 1-15 minutes. The presence of contrast within the myocardium at t=15 minutes comprises a positive signal, and hence for post-ischemic injury. Conversely, the absence of contrast signal at t=15 minutes indicates the absence of selectin expression, and the absence of post-ischemic condition.

It will be obvious to one skilled in the art that the optimal timepoint after agent administration at which contrast signal is assessed (also known as the dwell time) may be influenced by the total agent dose, patient body mass, and characteristics of the ultrasound scanner used, and may not be equal to 15 minutes in all cases. In general, it is desired that most to substantially all of the administered microbubbles have left the active circulation, by clearance or by binding to selectins in the target tissue, at the time at which the contrast signal is assessed.

Ratiometric methods for defining the presence of contrast within the myocardium at the dwell period are contemplated. Such analysis methods may be useful to obtain a more robust definition of positive contrast signal, or may be useful for improving the sensitivity of evaluation. For example, the signal within the myocardium at the dwell time may be normalized by that immediately after administration, or normalized by the signal within the left ventricular cavity. Such ratiometric methods may be performed on aligned images to yield a normalized image.

It will be obvious to one skilled in the art that many of the existing sonographic techniques for analyzing the heart are applicable to this method.

Example 11

Use of Targeted Contrast Agent for Detecting Post-ischemic Renal Injury by Molecular Imaging P-selectin is a molecular marker of post-ischemic injury in the kidney, and contrast agents targeting P-selectin can be used to detect the presence of P-selectin by molecular imaging. Microbubbles bearing TIM-1 are administered intravenously to a patient, and the contrast signal monitored by ultrasound imaging. Evaluation of the acquired contrast imaging data for the presence or absence of the disease may be performed as described in example 5.

Example 12

Use of Targeted Contrast Agent for Detecting Intestinal Inflammation by Molecular Imaging P-selectin is a molecular marker of bowel inflammation, and the contrast agents disclosed herein may be used to detect the presence and anatomical location of inflammatory lesions. For example, the extracellular domain of TIM-1 expressed as an cys-tag fusion protein is conjugated to IRDye800, a medical imaging contrast-producing agent used for optical imaging. The IRDye800 probe is administered to a patient with suspected inflammation of the bowel. The bowel is then imaged using a fluorescence detecting endoscope, and the presence or absence of P-selectin is determined from the fluorescent produced by P-selectin bound IRDye800.

Example 13

Use of Targeted Contrast Agent for Detecting Arterial Thrombosis by Molecular Imaging P-selectin is a molecular marker of activated platelets found in the context of arterial thrombosis, and molecular imaging with contrast agents disclosed here may be used to detect the presence and location of arterial thrombi. For example, microbubbles comprising the extracellular domain of TIM-1 expressed as an Fc fusion protein as a targeting ligand are administered to a patient with suspected arterial thrombosis. The wash-in and uptake of the microbubbles through the artery of interest is imaged and recorded by ultrasound imaging over 5-15 minutes. The contrast signal at each location within the artery at t=15 minutes is normalized by the signal at peak intensity on a pixel-by-pixel basis. A contrast threshold is defined (based on a baseline scan or scan of known healthy tissue) such that contrast signals above said threshold are considered contrast positive, and those below said threshold are considered contrast negative. The extent of arterial thrombosis is determined as the fraction of imaged area comprised of contrast-positive pixels.

Example 14

Use of Targeted Contrast Agent for Detecting Solid Tumors

Selectin expression is known to occur in some solid tumors. Microbubbles prepared as in Example 4 for may be used to identify the location of tumors as follows. A baseline scan of the patient's abdomen is perfomed and recorded. The patient is then administered the microbubble contrast agent as a bolus in physiological saline, and the microbubbles are allowed to accumulate for 10 minutes. A second scan of the abdomen is then performed, and regions of enhanced contrast, relative to baseline, are noted. Said imaging procedure is repeated at intervals of 1 week to 6 months in order to evaluate changes in tumor extent or phenotype in response to treatment.

Example 15

Use of TIM-1 Microbubble for Drug Delivery

Microbubbles bound to a drug and comprising the extracellular domain of TIM-1 as a targeting ligand are used to deliver said drug to P-selectin expressing cells in living animals. In this case, a target site is defined as a region within the body in which P-selectin is expressed. Drug-bearing microbubbles are administered intravenously to the subject, and allowed to accumulate at the target site for 25 minutes. Accumulation of drug-bearing microbubbles at the target site is monitored by ultrasound imaging. Release of the drug from the microbubble and into the P-selectin expressing cells is mediated by the application of high pressure acoustic energy, via a process generally referred to as sonoporation. Acoustic energy at 1.0 MHz, a duty cycle of 50%, and acoustic pressure of 500 kPa is applied transdcutaneously to the target site using an ultrasound-emitting device.

REFERENCES

Backer M V, Patel V, Jehning B T, Backer J M. Self-assembled "dock and lock" system for linking payloads to targeting proteins. *Bioconjug Chem.* 2006 July-August; 17(4):912-9.

Davidson B P, Kaufmann B A, Belcik J T, Xie A, Qi Y, Lindner J R. Detection of antecedent myocardial ischemia with multiselectin molecular imaging. *J Am Coll Cardiol.* 2012 Oct. 23; 60(17):1690-7.

Deshpande N, Lutz A M, Ren Y, Foygel K, Tian L, Schneider M, Pai R, Pasricha P J, Willmann J K. Quantification and monitoring of inflammation in murine inflammatory bowel disease with targeted contrast enhanced *US. Radiology.* 2012 January; 262(1):172-80.

Dimitroff C J, Lee J Y, Rafii S, Fuhlbrigge R C, Sackstein R. C D44 is a major E-selectin ligand on human hematopoietic progenitor cells. *J Cell Biol.* 2001 Jun. 11; 153(6): 1277-86.

Feshitan J A, Chen C C, Kwan J J, Borden M A. Microbubble size isolation by differential centrifugation. *J Colloid Interface Sci.* 2009 Jan. 15; 329(2):316-24.

Funovics M, Montet X, Reynolds F, Weissleder R, Josephson L. Nanoparticles for the optical imaging of tumor E-selectin. *Neoplasia.* 2005 October; 7(10):904-11.

Gratz S, Béhé M, Boerman O C, Kunze E, Schulz H, Eiffert H, O'Reilly T, Behr T M, Angerstein C, Nebendahl K, Kauer F, Becker W. (99m)Tc-E-selectin binding peptide for imaging acute osteomyelitis in a novel rat model. *Nucl Med Commun.* 2001 September; 22(9):1003-13.

Guenther F, von zur Muhlen C, Ferrante E A, Grundmann S, Bode C, Klibanov A L. An ultrasound contrast agent targeted to P-selectin detects activated platelets at supra-arterial shear flow conditions. *Invest Radiol.* 2010 October; 45(10):586-91.

Hariri G, Zhang Y, Fu A, et al. Radiation-Guided P-Selectin Antibody Targeted to Lung Cancer. *Annals of biomedical engineering.* 2008;36(5):821-830. doi:10.1007/s10439-008-9444-9.

Jin A Y, Tuor U I, Rushforth D, Filfil R, Kaur J, Ni F, Tomanek B, Barber P A. Magnetic resonance molecular imaging of post-stroke neuroinflammation with a P-selectin targeted iron oxide nanoparticle. *Contrast Media Mol Imaging.* 2009 November-December; 4(6):305-11.

Jin A Y, Tuor U I, Rushforth D, Filfil R, Kaur J, Ni F, Tomanek B, Barber P A. Magnetic resonance molecular imaging of post-stroke neuroinflammation with a P selectin targeted iron oxide nanoparticle. *Contrast Media Mol Imaging.* 2009 November-December; 4(6):305-11.

Klibanov A L, Rychak J J, Yang W C, Alikhani S, Li B, Acton S, Lindner J R, Ley K, Kaul S. Targeted ultrasound contrast agent for molecular imaging of inflammation in high-shear flow. *Contrast Media Mol Imaging.* 2006 November-December; 1(6):259-66.

Lindner J R, Song J, Christiansen J, Klibanov A L, Xu F, Ley K. Ultrasound assessment of inflammation and renal tissue injury with microbubbles targeted to P-selectin. *Circulation.* 2001 Oct. 23; 104(17):2107-12.

Nakamura I, Hasegawa K, Wada Y, Hirase T, Node K, Watanabe Y. Detection of early stage atherosclerotic plaques using PET and CT fusion imaging targeting P selectin in low density lipoprotein receptor-deficient mice. *Biochem Biophys Res Commun.* 2013 Mar. 29; 433(1):47-51.

Rodriguez-Manzanet R, DeKruyff R, Kuchroo V K, Umetsu D T. The costimulatory role of TIM molecules. *Immunol Rev.* 2009 May; 229(1):259-70.

Rouzet F, Bachelet-Violette L, Alsac J M, Suzuki M, Meulemans A, Louedec L, Petiet A, Jandrot-Perrus M, Chaubet F, Michel J B, Le Guludec D, Letourneur D. Radiolabeled fucoidan as a p-selectin targeting agent for in vivo imaging of platelet-rich thrombus and endothelial activation. *J Nucl Med.* 2011 September; 52(9):1433-40.

Rychak J J, Li B, Acton S T, Leppänen A, Cummings R D, Ley K, Klibanov A L. Selectin ligands promote ultrasound contrast agent adhesion under shear flow. *Mol Pharm.* 2006 September-October; 3(5):516-24.

Structural Genomics Consortium; China Structural Genomics Consortium; Northeast Structural Genomics Consortium, Gräslund S, Nordlund P, Weigelt J, Hallberg B M, Bray J, Gileadi O, Knapp S, Oppermann U, Arrowsmith C, Hui R, Ming J, dhe-Paganon S, Park H W, Savchenko A, Yee A, Edwards A, Vincentelli R, Cambillau C, Kim R, Kim S H, Rao Z, Shi Y, Terwilliger T C, Kim C Y, Hung L W, Waldo G S, Peleg Y, Albeck S, Unger T, Dym O, Prilusky J, Sussman J L, Stevens R C, Lesley S A, Wilson I A, Joachimiak A, Collart F, Dementieva I, Donnelly M I, Eschenfeldt W H, Kim Y, Stols L, Wu R, Zhou M, Burley S K, Emtage J S, Sauder J M, Thompson D, Bain K, Luz J, Gheyi T, Zhang F, Atwell S, Almo S C, Bonanno J B, Fiser A, Swaminathan S, Studier F W, Chance M R, Sali A, Acton T B, Xiao R, Zhao L, Ma L C, Hunt J F, Tong L, Cunningham K, Inouye M, Anderson S, Janjua H, Shastry R, Ho C K, Wang D, Wang H, Jiang M, Montelione G T, Stuart D I, Owens R J, Daenke S, Schütz A, Heinemann U, Yokoyama S, Büssow K, Gunsalus K C. Protein production and purification. *Nat Methods.* 2008 February; 5(2):135-46.

Villanueva F S, Lu E, Bowry S, Kilic S, Tom E, Wang J, Gretton J, Pacella J J, Wagner W R. Myocardial ischemic memory imaging with molecular echocardiography. *Circulation.* 2007 Jan. 23; 115(3):345-52.

Waugh, David S. "An Overview of Enzymatic Reagents for the Removal of Affinity Tags." *Protein expression and purification* 80.2 (2011): 283-293.

Xie A, Belcik T, Qi Y, Morgan T K, Champaneri S A, Taylor S, Davidson B P, Zhao Y, Klibanov A L, Kuliszewski M A, Leong-Poi H, Ammi A, Lindner J R. Ultrasound-mediated vascular gene transfection by cavitation of endothelial-targeted cationic microbubbles. *JACC Cardiovasc Imaging.* 2012 December; 5(12):1253-62.

Zinn K R, Chaudhuri T R, Smyth C A, Wu Q, Liu H G, Fleck M, Mountz J D, Mountz J M. Specific targeting of activated endothelium in rat adjuvant arthritis with a 99mTc-radiolabeled E-selectin-binding peptide. *Arthritis Rheum.* 1999 April; 42(4):641-9.

Klaveness et al., U.S. Pat. No. 6,680,047.
Glajch et al., U.S. Pat. No. 6,254,852.
Unger et al., U.S. Pat. No. 6,139,819.
Lindner et al., International (PCT) Publication No. WO 20080131217 A1.
Bettinger et al., International (PCT) Publication No. WO 2012020030 A1.
Barrett et al., U.S. Pat. No. 5,643,873.
Fukuda et al., U.S. Pat. No. 7,470,658.
Winter et al., U.S. Pat. No. 5,624,821.
Sanicola-Nadel et al., U.S. Pat. No. 6,664,385.
Bluestone et al., U.S. Pat. No. 5,885,573.
Idusogie et al., U.S. Pat. No. 6,194,551.

What is claimed is:

1. A composition for molecular imaging of selectins, comprising an ultrasound contrast agent comprising gas-filled microbubbles associated with a targeting ligand by means of a covalent chemical bond with succinimidyl-4-N-maleimidomethyl cyclohexane-1-carboxylate (SMCC) crosslinker (SMCC), wherein said targeting ligand comprises the amino acid sequence as set forth in SEQ ID NO: 2 or SEQ ID NO: 3, wherein the sequence further comprises a fusion protein comprising human Fc.

2. The composition of claim 1 wherein the sequence further comprises a fusion protein comprising a terminal cysteine.

3. The composition of claim 1 wherein the targeting ligand further comprises an intervening polymer spacer connecting the targeting ligand to the microbubble.

4. The composition of claim 1 wherein said selectin is P-selectin.

5. The composition of claim 1 wherein said selectin is E-selectin.

* * * * *